United States Patent
Podhajsky

(10) Patent No.: US 8,123,744 B2
(45) Date of Patent: Feb. 28, 2012

(54) WOUND MEDIATING DEVICE

(75) Inventor: Ronald J. Podhajsky, Boulder, CO (US)

(73) Assignee: Covidien AG (CH)

( * ) Notice: Subject to any disclaimer, the term of this patent is extended or adjusted under 35 U.S.C. 154(b) by 1141 days.

(21) Appl. No.: 11/511,654

(22) Filed: Aug. 29, 2006

(65) Prior Publication Data

US 2008/0125742 A1    May 29, 2008

(51) Int. Cl.
*A61B 18/14* (2006.01)

(52) U.S. Cl. ........................................................... 606/41

(58) Field of Classification Search .............. 606/32–42, 606/213–215
See application file for complete search history.

(56) References Cited

U.S. PATENT DOCUMENTS

| | | | |
|---|---|---|---|
| 2,708,933 A | 5/1955 | August | |
| 2,828,747 A | 4/1958 | August | |
| 3,434,476 A | 3/1969 | Shaw et al. | |
| 3,569,661 A | 3/1971 | Ebeling | |
| 3,595,239 A | 7/1971 | Petersen | |
| 3,692,973 A | 9/1972 | Oku et al. | |
| 3,699,967 A | 10/1972 | Anderson | |
| 3,832,513 A | 8/1974 | Klasson | |
| 3,838,242 A | 9/1974 | Goucher | |
| 3,903,891 A | 9/1975 | Brayshaw | |
| 3,970,088 A | 7/1976 | Morrison | |
| 3,987,795 A | 10/1976 | Morrison | |
| 4,014,343 A | 3/1977 | Esty | |
| 4,019,925 A | 4/1977 | Nenno et al. | |
| 4,040,426 A | 8/1977 | Morrison, Jr. | |
| 4,041,952 A | 8/1977 | Morrison, Jr. et al. | |
| 4,043,342 A | 8/1977 | Morrison, Jr. | |
| 4,057,064 A | 11/1977 | Morrison, Jr. et al. | |
| 4,060,088 A | 11/1977 | Morrison, Jr. et al. | |
| 4,209,018 A | 6/1980 | Meinke et al. | |
| 4,237,877 A * | 12/1980 | Boehler | 128/204.15 |
| 4,242,562 A | 12/1980 | Karinsky et al. | |
| 4,311,145 A | 1/1982 | Esty et al. | |
| 4,492,231 A | 1/1985 | Auth | |
| 4,492,845 A | 1/1985 | Kljuchko et al. | |
| 4,545,375 A | 10/1985 | Cline | |
| 4,577,637 A | 3/1986 | Mueller, Jr. | |
| 4,601,701 A | 7/1986 | Mueller, Jr. | |
| 4,665,906 A | 5/1987 | Jervis | |
| 4,708,137 A | 11/1987 | Tsukagoshi | |
| 4,708,861 A * | 11/1987 | Popescu et al. | 424/1.21 |
| 4,711,238 A | 12/1987 | Cunningham | |

(Continued)

FOREIGN PATENT DOCUMENTS

DE    3710489    11/1987

(Continued)

OTHER PUBLICATIONS

Grund et al., "Endoscopic Argon Plasma . . . Flexible Endoscopy" Endoscopic Surgery and Allied Technologies, No. 1, vol. 2, pp. 42-46 (Feb. 1994).

(Continued)

*Primary Examiner* — Michael Peffley
*Assistant Examiner* — Ronald Hupczey, Jr.

(57) ABSTRACT

A wound mediating device is provided to facilitate healing of tissue. The wound mediating device includes a wound mediating substance encapsulated in microbubbles which are suspended in a slurry. The slurry is stored in, and supplied from, any suitable container configured for use with a surgical instrument capable of propelling the slurry towards tissue.

12 Claims, 7 Drawing Sheets

U.S. PATENT DOCUMENTS

| | | | |
|---|---|---|---|
| 4,728,322 A | 3/1988 | Walker et al. | |
| 4,732,556 A | 3/1988 | Chiang et al. | |
| 4,753,223 A | 6/1988 | Bremer | |
| 4,766,046 A * | 8/1988 | Abra et al. | 424/450 |
| 4,781,175 A | 11/1988 | McGreevy et al. | |
| 4,817,613 A | 4/1989 | Jaraczewski et al. | |
| 4,822,557 A | 4/1989 | Suzuki et al. | |
| 4,864,824 A | 9/1989 | Gabriel et al. | |
| 4,890,610 A | 1/1990 | Kirwan, Sr. et al. | |
| 4,901,719 A | 2/1990 | Trenconsky et al. | |
| 4,901,720 A | 2/1990 | Bertrand | |
| 4,931,047 A | 6/1990 | Broadwin et al. | |
| 4,955,863 A | 9/1990 | Walker et al. | |
| 5,015,227 A | 5/1991 | Broadwin et al. | |
| 5,041,110 A | 8/1991 | Fleenor | |
| 5,061,268 A | 10/1991 | Fleenor | |
| 5,061,768 A | 10/1991 | Kishimoto et al. | |
| 5,067,957 A | 11/1991 | Jervis | |
| 5,088,997 A | 2/1992 | Delahuerga et al. | |
| 5,098,430 A | 3/1992 | Fleenor | |
| 5,108,389 A | 4/1992 | Cosmescu | |
| RE33,925 E | 5/1992 | Bales et al. | |
| 5,122,138 A | 6/1992 | Manwaring | |
| D330,253 S | 10/1992 | Burek | |
| 5,152,762 A | 10/1992 | McElhenney | |
| 5,160,334 A | 11/1992 | Billings et al. | |
| 5,163,935 A | 11/1992 | Black et al. | |
| 5,195,959 A | 3/1993 | Smith | |
| 5,195,968 A | 3/1993 | Lundquist et al. | |
| 5,207,675 A | 5/1993 | Canady | |
| 5,217,457 A | 6/1993 | Delahuerga et al. | |
| 5,221,259 A * | 6/1993 | Weldon et al. | 604/96.01 |
| 5,234,457 A | 8/1993 | Andersen | |
| 5,242,438 A | 9/1993 | Saadatmonesh et al. | |
| 5,244,462 A | 9/1993 | Delahuerga et al. | |
| 5,248,311 A | 9/1993 | Black et al. | |
| 5,256,138 A | 10/1993 | Burek et al. | |
| RE34,432 E | 11/1993 | Bertrand | |
| 5,292,320 A | 3/1994 | Brown et al. | |
| 5,306,238 A | 4/1994 | Fleenor | |
| 5,312,333 A * | 5/1994 | Churinetz et al. | 604/57 |
| 5,324,283 A | 6/1994 | Heckele | |
| 5,330,469 A | 7/1994 | Fleenor | |
| RE34,780 E | 11/1994 | Trenconsky et al. | |
| 5,366,456 A | 11/1994 | Rink et al. | |
| 5,370,649 A | 12/1994 | Gardetto et al. | |
| 5,380,317 A | 1/1995 | Everett et al. | |
| 5,389,390 A | 2/1995 | Kross | |
| 5,476,461 A | 12/1995 | Cho et al. | |
| 5,496,308 A | 3/1996 | Brown et al. | |
| 5,537,499 A | 7/1996 | Brekke | |
| 5,620,439 A | 4/1997 | Abela et al. | |
| 5,653,689 A | 8/1997 | Buelna et al. | |
| 5,662,621 A | 9/1997 | Lafontaine | |
| 5,669,904 A | 9/1997 | Platt, Jr. et al. | |
| 5,669,907 A | 9/1997 | Platt, Jr. et al. | |
| 5,688,261 A | 11/1997 | Amirkhanion et al. | |
| 5,698,189 A * | 12/1997 | Rowe et al. | 424/78.08 |
| 5,700,260 A | 12/1997 | Cho et al. | |
| 5,707,402 A * | 1/1998 | Heim | 607/88 |
| 5,716,365 A | 2/1998 | Goicoechea et al. | |
| 5,720,745 A | 2/1998 | Farin et al. | |
| 5,782,860 A | 7/1998 | Epstein et al. | |
| 5,782,896 A | 7/1998 | Chen et al. | |
| 5,797,920 A | 8/1998 | Kim | |
| 5,800,500 A | 9/1998 | Spelman et al. | |
| 5,800,516 A | 9/1998 | Fine et al. | |
| 5,821,664 A | 10/1998 | Shahinpoor | |
| 5,836,944 A | 11/1998 | Cosmescu | |
| 5,848,986 A | 12/1998 | Lundquist et al. | |
| 5,855,475 A | 1/1999 | Fujio et al. | |
| 5,908,402 A | 6/1999 | Blythe | |
| 5,964,714 A | 10/1999 | Lafontaine | |
| 5,972,416 A | 10/1999 | Reimels et al. | |
| 6,039,736 A | 3/2000 | Platt | |
| 6,080,183 A | 6/2000 | Tsugita et al. | |
| 6,102,940 A | 8/2000 | Robichon et al. | |
| 6,117,167 A | 9/2000 | Goicoechea et al. | |
| 6,139,519 A | 10/2000 | Blythe | |
| 6,149,648 A | 11/2000 | Cosmescu | |
| 6,197,026 B1 | 3/2001 | Farin et al. | |
| 6,213,999 B1 | 4/2001 | Platt, Jr. et al. | |
| 6,264,650 B1 | 7/2001 | Hovda et al. | |
| 6,475,217 B1 | 11/2002 | Platt | |
| 6,558,383 B2 | 5/2003 | Cunningham et al. | |
| 6,602,249 B1 | 8/2003 | Stoddard | |
| 6,616,660 B1 | 9/2003 | Platt | |
| 6,666,865 B2 | 12/2003 | Platt | |
| 6,852,112 B2 | 2/2005 | Platt | |
| 6,911,029 B2 | 6/2005 | Platt | |
| 7,033,353 B2 | 4/2006 | Stoddard | |
| 7,217,254 B2 * | 5/2007 | Kirwan et al. | 604/82 |
| 7,544,177 B2 * | 6/2009 | Gertner | 604/24 |
| 2002/0022838 A1 | 2/2002 | Cunningham et al. | |
| 2003/0093073 A1 | 5/2003 | Platt | |
| 2003/0144654 A1 | 7/2003 | Hilal | |
| 2004/0167512 A1 | 8/2004 | Stoddard | |
| 2005/0015086 A1 | 1/2005 | Platt | |
| 2005/0171528 A1 | 8/2005 | Sartor | |
| 2005/0197658 A1 | 9/2005 | Platt | |
| 2006/0052771 A1 | 3/2006 | Sartor | |
| 2006/0088581 A1 | 4/2006 | Blaszczykiewicz et al. | |

FOREIGN PATENT DOCUMENTS

| | | |
|---|---|---|
| DE | 4139029 | 6/1993 |
| DE | 4326037 | 2/1995 |
| DE | 9117019 | 4/1995 |
| DE | 9117299 | 4/2000 |
| DE | 19848784 | 5/2000 |
| DE | 29724247 | 8/2000 |
| EP | 956827 | 11/1999 |
| EP | 1561430 | 8/2005 |
| FR | 1340509 | 9/1963 |
| GB | L014995 | 12/1965 |
| JP | 61-159953 | 7/1986 |
| SU | 1438745 | 11/1988 |
| WO | WO91/13593 | 9/1991 |
| WO | WO93/03678 | 3/1993 |
| WO | WO96/27337 | 9/1996 |
| WO | WO99/015091 | 4/1999 |

OTHER PUBLICATIONS

Farin et al., "Technology of Argon Plasma . . . Endoscopic Applications" Endoscopic Surgery and Allied Technologies, No. 1, vol. 2, pp. 71-77 (Feb. 1994).

Brand et al., "Electrosurgical Debulking of Ovarian Cancer: A New Technique Using the Argon Beam Coagulator" Gynecologic Oncology 39 pp. 115-118 (1990).

Hernandez et al., "A Controlled Study of the Argon Beam Coagultor for Partial Nephrectomy" The Journal of Urology, vol. 143, May (J. Urol. 143: pp. 1062-1065, 1990).

Ward et al., "A Significant New Contribution to Radical Head and Neck Surgery" Arch Otolaryngology, Head and Neck Surg., vol. 115 pp. 921-923 (Aug. 1989).

Mark H. Mellow, "The Role of Endoscopic Laser Therapy in Gastrointestinal Neoplasms" Advanced Therapeutic Endoscopy, pp. 17-21, 1990.

Silverstein et al., "Thermal Coagulation Therapy for Upper Gatrointestinal Bleeding" Advanced Therapeutic Endoscopy, pp. 79-84, 1990.

Waye et al., "Endoscopic Treatment Options" Techniques in Therapeutic Endoscopy, pp. 1.7-1.15, 1987.

International Search Report 01102843.8-2305, dated May 15, 2001.
International Search Report PCT/US98/19284, dated Jan. 14, 1999.
European Searh Report EP 05 00 2257, dated Jun. 1, 2005.

* cited by examiner

WOUND MEDIATING DEVICE

BACKGROUND

1. Technical Field

The present disclosure relates to wound mediating devices. More particularly, the present disclosure relates to a wound mediating device using a pressurized fluid to serve as a propellant for the wound mediating substances.

2. Background of Related Art

Many surgical procedures are enhanced by the use of wound mediating substances to assist in the healing of tissue. The substances may include blood clotting factors, wound closing adhesives, growth factors, interleukins, cytokines, inflammatory mediating factors, chemokines, matrix-metalloproteinase or other biochemicals known to mediate wound healing. These wound mediating substances are typically expressed naturally in tissue after the surgery and wound healing can be enhanced through topical application of these substances. Application generally includes direct, manual application of the mediating substances to the appropriate area of the tissue.

Various surgical instruments are known for treating tissue. For example, surgical instruments used for tissue division, dissection, ablation, or for arresting blood loss and coagulation are well-known. In a particular application, for example a coagulation instrument, an electrode is used in conjunction with a heated probe to arrest bleeding. However, since the probe must come into close contact with the tissue, the probe may adhere to the tissue during probe removal and possibly cause repeat bleeding.

Some prior art devices include a tube-like coagulation instrument in which an ionizable gas is supplied to the instrument and ionized by the electrode. The atmosphere of ionized gases is beneficial because it helps focus and arc energy adjacent the electrode, displace oxygen from the area, and reduce oxidative stress of the tissue. The gas is propelled from the instrument toward the tissue.

However, energy based medical devices often rely on the body's own wound healing process as an integral element of their use. As noted above, wound mediating substances are often manually applied to the tissue after the surgery to mediate wound healing. This, however, requires direct contact of the applicator, i.e., wand, brush, probe, etc. to the tissue which may re-injure the previously operated on tissue.

SUMMARY

There is disclosed a wound mediating device which generally includes a container, a slurry disposed with the container, a plurality of microbubbles suspended in the slurry, and a wound mediating substance encapsulated in the microbubbles. The device may also include a source of pressurized gas that directs a gas stream towards a tissue wound and associated with the container such that the slurry is movable into the gas stream.

The wound mediating substances may generally include an antibacterial agent, an antifungal agent, an anti-inflammatory agent, an antimicrobial agents, an antiseptics, a chemotherapy agent, a coagulant, a hormone, a cancer tumor adjuvant, a local anesthetic, a pain mediator, a vasoconstrictor, a wound closing adhesive, a blood clotting factor, a growth factor, an interleukin, a cytokines, an inflammatory mediating factor, a chemokine and a matrix-metalloproteinase.

The microbubbles may generally include one or more liposomes, micelles, and microspheres.

In one embodiment, there may also be provided a surgical instrument capable of providing the source of pressurized gas. In a particular embodiment, the surgical instrument is an electrosurgical instrument. In this embodiment, the source of pressurized gas is a source of pressurized argon gas.

In a particular embodiment, the container is removably attached to the surgical instrument.

There is also provided a wound mediating surgical instrument including a surgical instrument having an internal chamber. A fluid pressure source is attached to the surgical instrument and is in fluid communication with the internal chamber such that the fluid pressure source operable to provide a fluid stream through the internal chamber. In this embodiment, a wound mediating device is attached to the surgical instrument. The wound mediating device includes a container, a slurry disposed within the container, a plurality of microbubbles suspended within the slurry and a wound mediating substance that may be encapsulated within the microbubbles. In this embodiment, the slurry contained within the container is introduced into the internal chamber of the surgical instrument downstream of the fluid pressure source.

In this embodiment, the wound mediating device may also be removably attached to the surgical instrument.

In a particular embodiment, the surgical instrument is an electrosurgical instrument and the gas is argon.

There is also disclosed a method of treating a wound during surgery which includes encapsulating a wound mediating substance in microbubbles and suspending the microbubbles in a slurry. The slurry is disposed within a container and is drawn out of the container and into a fluid stream which is then directed towards a wound in tissue. The method may also include passing the fluid stream through a surgical instrument which provides a fluid pressure source for the fluid stream.

In this particular embodiment, directing the fluid stream may include propelling with a pressurized gas.

In some embodiments, the pressurized gas and the slurry are operatively combinable within a wound mediating instrument.

In some embodiments, the wound mediating substance is at least one of an antibacterial agent, an antifungal agent, an anti-inflammatory agent, an antimicrobial agents, an antiseptics, a chemotherapy agent, a coagulant, a hormone, a cancer tumor adjuvant, a local anesthetic, a pain mediator, a vasoconstrictor, a wound closing adhesive, a blood clotting factor, a growth factor, an interleukin, a cytokines, an inflammatory mediating factor, a chemokine and a matrix-metalloproteinase.

In some embodiments, the source of pressurized gas is argon.

DESCRIPTION OF THE DRAWINGS

Various embodiments of the presently disclosed wound mediating device are disclosed herein with reference to the drawings, wherein.

DETAILED DESCRIPTION

Embodiments of the presently disclosed wound mediating device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
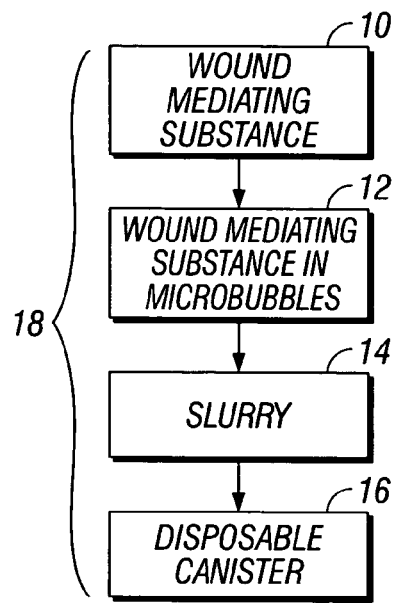
FIG. 1 is a flowchart of a wound mediating substance being stored in a canister.

Referring initially to FIG. 1, a method of assembling a wound mediating substance into a form that can be readily applied to a surgical instrument assisted by a fluid flow system is illustrated. An appropriate wound mediating substance 10 is chosen for use in the supply. In a particular method wound mediating substance 10 is suitably prepared and is encapsulated in a carrier material, such as, for example, microbubbles 12. The wound mediating substance 10, carried within microbubbles 12, are then mixed with a slurry 14 to form a composition suitable to be injected into a fluid flow stream. Once the composition has properly been prepared it can be stored in any suitable container for use. In a particular embodiment, the composition is stored in a disposable and/or removable canister 16. Canister 16 is particularly configured for use with various surgical instruments and can assume various forms allowing it to be removably attached to the surgical instruments. Additionally, canister 16 may be coded by color or other means to identify the contents contained within canister 16. Further, canister 16 may be provided with unique attachment structures such that only particular canisters 16 will function with certain surgical instruments.

Wound mediating substances 10 can take on any suitable form for use in connection with wound or tissue healing processes, and/or be applied in amounts sufficient to have a beneficial affect on one or more wounds. Non-limiting examples of wound mediating substances includes active agents such as antibacterial agents, antifungal agents, anti-inflammatory agents, antimicrobial agents, antiseptics, chemotherapy agents, coagulants, hormones, cancer tumor adjuvants, local anesthetics, pain mediators, vasoconstrictors, and combinations thereof. Furthermore, wound mediating substances 10 can include any individual or combination of blood clotting factors, wound closing adhesives, growth factors, interleukins, cytokines, inflammatory mediating factors, chemokines, matrix-metalloproteinase, or any suitable biochemicals to mediate wound healing. It is envisioned that combinations of these wound mediating substances can be used.

Non-limiting examples of antimicrobial agents include bacitracin, cerium nitrate-silver sulphadiazine, chlorhexidine, gentamicin, mafenide, mupirocin, nitrofurazone, norfloxacin, povidone iodine, sodium hypochloride, silver sulphadiazine, silver nitrate solution 0.5%, and/or other suitable antimicrobial used in wounds, and/or combinations thereof.

Non-limiting examples of antibacterial agents include ampicillin, cephalosporin, erythromycin, penicillin, polysporin, neosporin, tetracycline, and/or other suitable antibacterial used in wounds, and/or combinations thereof.

Non-limiting examples of chemotherapy agents include anthracyclines, cetuximab, cisplatin, cyclophosphamide, dexamethasone, diethylstilbestrol, doxorubicin, etoposide, 5-fluorouracil, methotrexate, paclitaxel (taxol), tamoxifen, topotecan, vincristine, and/or any other suitable chemotherapy agent, and/or combinations thereof.

Non-limiting examples of local anesthetics include benzocaine, dibucaine, dyclonine hydrochloride, lidocaine, pramoxine hydrochloride, tetracaine and/or any suitable local anesthetic and/or combinations thereof. It is envisioned that the salts and base forms of the esters and amides of these anesthetics can be suitable for use in accordance with the present disclosure. The local anesthetics can be administered by a variety of routes, and applied in amounts suitable to act on the nervous system and/or on nerve fiber.

Non-limiting examples of vasoconstrictors include antihistamines, adrenalin, angiotensins, arginine vasopressin, asymmetric dimethylarginine, caffeine, catecholamines, decongestants, endothelins, naphazoline, oxymetazoline, pseudoephadrine, norepinephrine, phenylephrine, thromboxane, or any composition capable of causing the narrowing of the blood vessels, and/or combinations thereof. Vasoconstrictors can be applied in amounts suitable to demonstrate vasoconstrictive activity.

Non-limiting examples of clotting factors include fibrin, fibrinogen, plasminogen, thrombospondin, or any suitable factors involved in the clotting cascade. Clotting factor can be applied in amounts suitable to demonstrate or facilitate blood clotting activity.

Non-limiting examples of cancer tumor adjuvants include taxanes, herceptin, trastuzamab, chemotherapy agents, hormones, and/or combinations of these agents. Cancer tumor adjuvants can be applied in amounts suitable to eradicate and/or reduce microscopic disease in the body, including portions of the body that do not have a tumor. Additional cancer tumor adjuvants include alpha-lipoic acid, arginine, carotenoids, cimetidine, clodronate, coenzyme Q10 and statin drugs, conjugated linoleic acid, cyclooxygenase-2 Inhibitors, berberine containing herbs, feverfew, ginger, green tea, curcumin, dimethyl sulfoxide, essential fatty acids, garlic, glutamine, inositol hexaphosphate, lactoferrin, melatonin, N-acetyl-cysteine, selenium, silibinin, soy, theanine, vitamin A, vitamin C, vitamin D, vitamin E and vitamin K, and/or combinations of these cancer tumor adjuvants.

Non-limiting examples of adhesives include cyanoacrylates, and/or other suitable adhesives used for wound closure or tissue coagulation, and combinations thereof. In embodiments, INDERMIL® brand topical skin adhesive from Tyco Healthcare LP may be used as a suitable adhesive. This adhesive can be applied in amounts sufficient to seal and/or close wounds. It is envisioned that the application of skin adhesive can promote wound closure by bonding two or more portions of skin together. Accordingly, adhesive can be applied in amounts suitable to bind portions of tissue.

Non-limiting examples of growth factors suitable for use in accordance with the present disclosure include fibroblast growth factors (FGFs), endothelial growth factors (VEGFs), transforming growth factors (TGFs), platelet derived growth factors (PDGFs), nerve growth factor (NGF), or any other growth factor that influences wound healing, and/or combinations thereof.

In addition to those wound mediating substances specifically described hereinabove, any other suitable mediators capable of influencing wound healing are specifically contemplated herein.

It is envisioned that the wound mediating substances in accordance with the present disclosure can be incorporated into any suitable carrier or medium. For example, suitable wound mediating substances can be incorporated into microbubbles. Microbubbles can include any suitable delivery system which encapsulates a wound mediating substance. It is envisioned that the carrier can be microbubbles such as surfactant aggregates such as those selected to facilitate drug targeting, liposomes, micelles, microspheres, and/or combinations thereof. For example, wound mediating substance may be incorporated into any suitable liposome, micelle, and/or microsphere delivery system.

Liposomes are microscopic vesicles having a lipid wall including a lipid bilayer, and can be used as drug delivery systems in accordance with the present disclosure. In embodiments, such liposome formulations may be used for poorly soluble or insoluble active agents. Liposomal preparations for use in the present disclosure can include cationic, anionic, and neutral preparations. One non-limiting example of a suitable cationic liposomes is N[1-2,3-dioleyloxy)propyl]-N,N,N-triethylammonium (DOTMA) liposomes. Similarly, non-limiting examples of suitable anionic and neutral liposomes include phosphatidyl choline, cholesterol, phosphatidyl ethanolamine, dioleoylphosphatidyl choline (DOPC), dioleoylphosphatidyl glycerol (DOPG), and dioleoylphoshatidyl ethanolamine (DOPE), and combinations thereof. In some embodiments, these materials can also be mixed with DOTMA in appropriate ratios.

As used herein, micelles include surfactant molecules arranged so that their polar headgroups form an outer spherical shell, while their hydrophobic, hydrocarbon chains are oriented towards the center of the sphere, forming a core. Non-limiting examples of surfactants useful for forming micelles include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethylammonium bromide, tetradecyltrimethylammonium bromide, tetradecyltrimethylammonium chloride, dodecylammonium chloride, polyoxyl 8 dodecyl ether, polyoxyl 12 dodecyl ether, nonoxynol 10, nonoxynol 30, and combinations thereof. Micelle formulations can be used in conjunction with the present disclosure either by incorporation into wound mediating supply 18, or into a microbubble to be applied to the body surface.

In some embodiments, the microbubbles include microspheres suitable for use as drug delivery systems. Like liposomes and micelles, microspheres encapsulate a wound mediating substance, or formulation thereof. Microspheres are generally, although not necessarily, formed from synthetic or naturally occurring biocompatible polymers, but may also be comprised of charged lipids such as phospholipids. In embodiments, biodegradable microspheres prepared from natural and synthesized polymers used in drug delivery systems are suitable for use in accordance with the present disclosure. It is envisioned that the microspheres are preselected to, among other things, control the rate at which a drug is released to the body, control triggered release, and/or control targeted delivery.

Surfactant aggregates can be selected to facilitate drug targeting such as active and/or passive targeting. Further, the surfactant aggregates can be preselected to facilitate controlled release, triggered release, and/or targeted delivery such that the wound mediating substance is efficacious. For example, in some embodiments, a wound mediating substance and/or active ingredient in inert form may be combined or incorporated into a carrier such as a microspere. When the carrier ruptures, the inert active ingredient may become active and capable of acting as a wound mediating substance. It is envisioned that the rupturing of the carrier and/or the activation of an inert active ingredient can be controlled such as through the application of energy thereto. For example, ultrasound, heat, light, temperature variation, and/or combinations thereof can be applied to the carrier to rupture the surface thereof and/or activate the wound mediating substance therein. It is also envisioned that the carrier can be ruptured, and/or an inert wound mediating substance activated by an increase or decrease in pH around the surface of the carrier and/or wound mediating substance.

In some embodiments, the wound mediating substance may be provided with a pharmaceutically acceptable topical carrier. In this regard, the wound mediating substance/carrier formulation may be in any form suitable for application to the body surface. Non-limiting forms suitable for application to the body include cream, lotion, solution, gel, hydrogel, ointment, paste, or the like, and combinations thereof. Such formulations may also include liposomes, micelles, and/or microspheres. Such formulations may be aqueous, i.e., contain water, or may be nonaqueous and optionally used in combination with an overlayer. Such formulations can also include emulsions.

Figure 2:
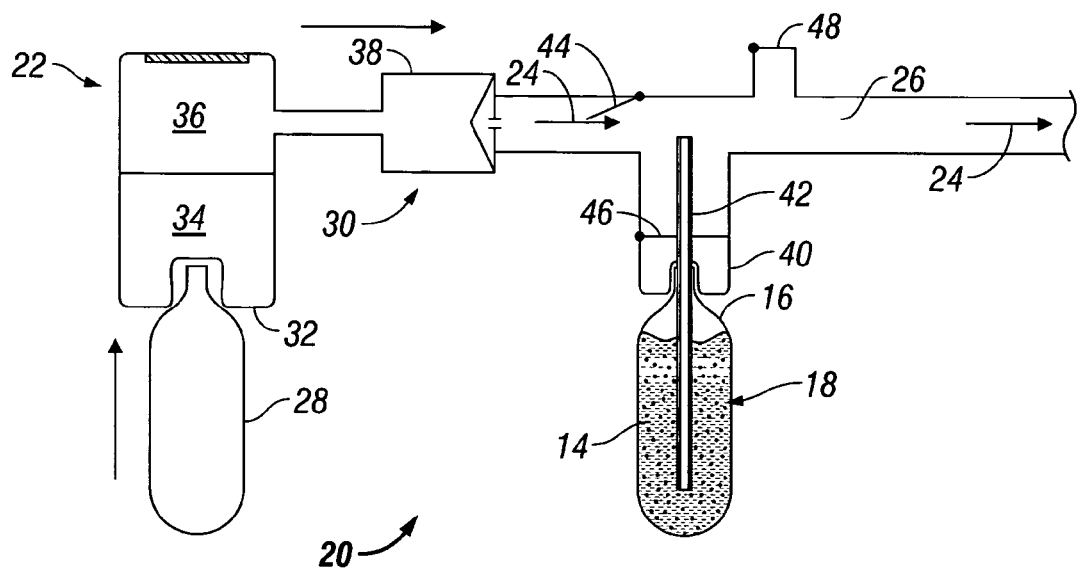
FIG. 2 is a schematic view of a wound mediating device according to one embodiment of the present disclosure.
Figure 3:
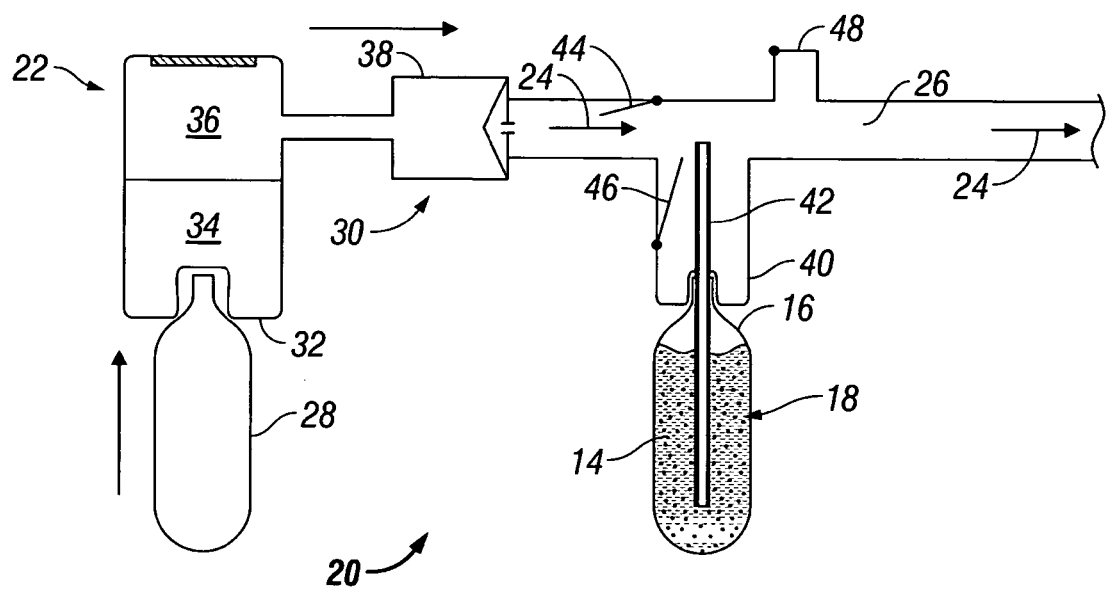
FIG. 3 is a schematic view similar to FIG. 2 during initial operation.
Figure 4:
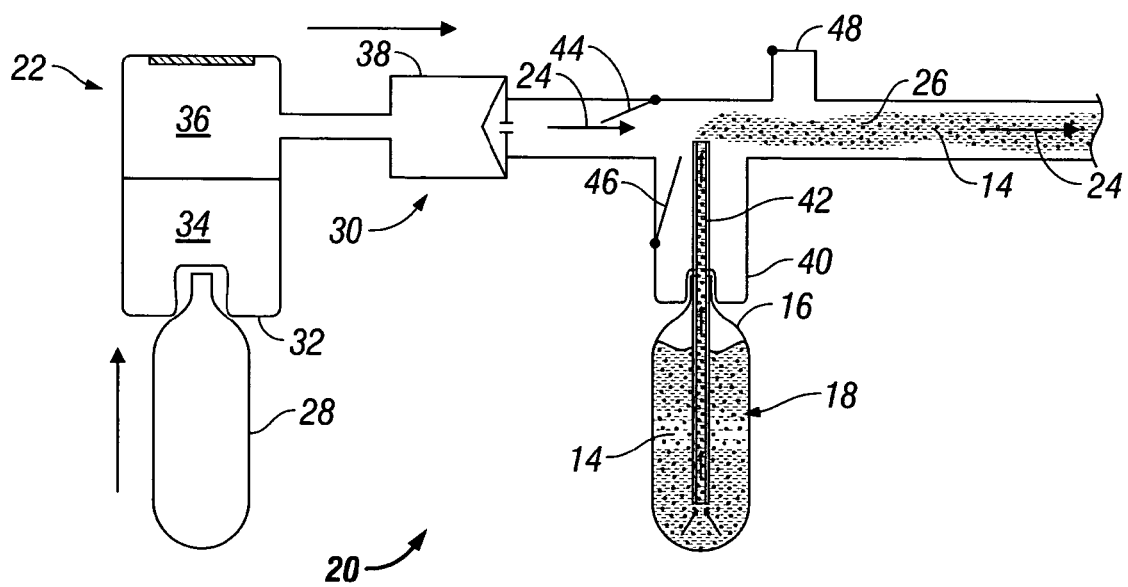
FIG. 4 is a schematic view similar to FIG. 3 with a slurry being ejected from the device.

Referring now to FIGS. 2-4, and initially with regard to FIG. 2, a wound mediating device 20, including wound mediating supply 18, will now be described. Wound mediating device 20 generally includes a pressure source 22 and wound mediating supply 18. Pressure source 22 provides a fluid flow stream 24 to propel slurry 14 contained in wound mediating supply 18 towards tissue. In a particular embodiment, fluid flow stream 24 moves through a fluid flow channel 26.

Wound mediating device 20 can be a self-contained instrument or can be connected to any generic surgical instrument utilizing a fluid flow system. As illustrated in FIG. 2, a generic surgical instrument may be represented by housing 30. A pressure supply 28 may be associated with the surgical instrument to provide pressure source 22 to the system. Pressure supply 28 can be an external source, for example any external source of fluid pressure utilized with surgical instruments, or maybe removably attached to the surgical instrument. As shown, a mount 32 is used to affix pressure supply 28 to housing 30.

In this embodiment, a high pressure system 34 and a low-pressure system 36 may be associated with housing 30 depending upon the nature the surgical device being used therewith. As is common with fluid assisted surgical instruments, a flow regulator 38 may also be provided as part of the system.

As noted hereinabove, wound mediating device 20 includes wound mediating supply 18. In a particular embodiment, wound mediating supply 18 is removably affixed to housing 30 by means of a mount 40. A transfer tube 42 may be associated with either canister 16 or housing 30 to provide a vehicle for transferring slurry 14 contained in canister 16 into fluid flow stream 24.

As is common with fluid-assisted surgical instruments, wound mediating device 20 may have a first valve 44 for controlling the flow of pressure from pressure supply 22 through fluid flow channel 26. Wound mediating device 20 may include a second valve 46 for controlling the flow of slurry 14 into fluid flow channel 26. Additionally, wound mediating device 20 may also include an overpressure relief valve 48 to assist in regulating the fluid flow stream 24 provided by pressure supply 28.

Referring now to FIGS. 2-4, initially, pressure supply 28 is mounted to mount 32 and wound mediating supply 18 is mounted to mount 40 of wound mediating device 20. Wound mediating device 20 is then operated to provide fluid flow stream 24 through fluid flow channel 26. In a particular embodiment this is accomplished by opening first valve 44. Depending upon the nature the application the fluid flow may include a gas, such as for example, argon gas utilized in conjunction with electrosurgical instruments. However, as noted above, wound mediating device 20 may be a stand-alone instrument utilized in conjunction with various surgical procedures.

During, or after completion of, the surgical procedure, second valve 46 is opened to provide a fluid flow stream 24 relative to wound mediating supply 18. Specifically, fluid flow stream 24 passes over transfer tube 42 to draw slurry 14 out of canister 16 and into flow stream 24 in a manner similar to that accomplished in other devices, such as, for example paint spray guns, etc. By regulating the opening of valve 46 the appropriate amount of slurry 14 can be metered into fluid flow stream 24. Thus, in this manner fluid flow stream 24 acts as a propellant to propel slurry 14, containing wound mediating substance 10 encapsulated in microbubbles, towards the tissue to facilitate healing of the tissue.

Wound mediating device 20 provides means of applying a wound mediating substance 10 to tissue without directly contacting the tissue with a physical or mechanical applicator of wound mediating substance 10. This ensures that the tissue at the wound site is not contaminated by the external applicator and that the external applicator does not do additional undesired damage to the tissue after the surgery has been completed.

Figure 5:
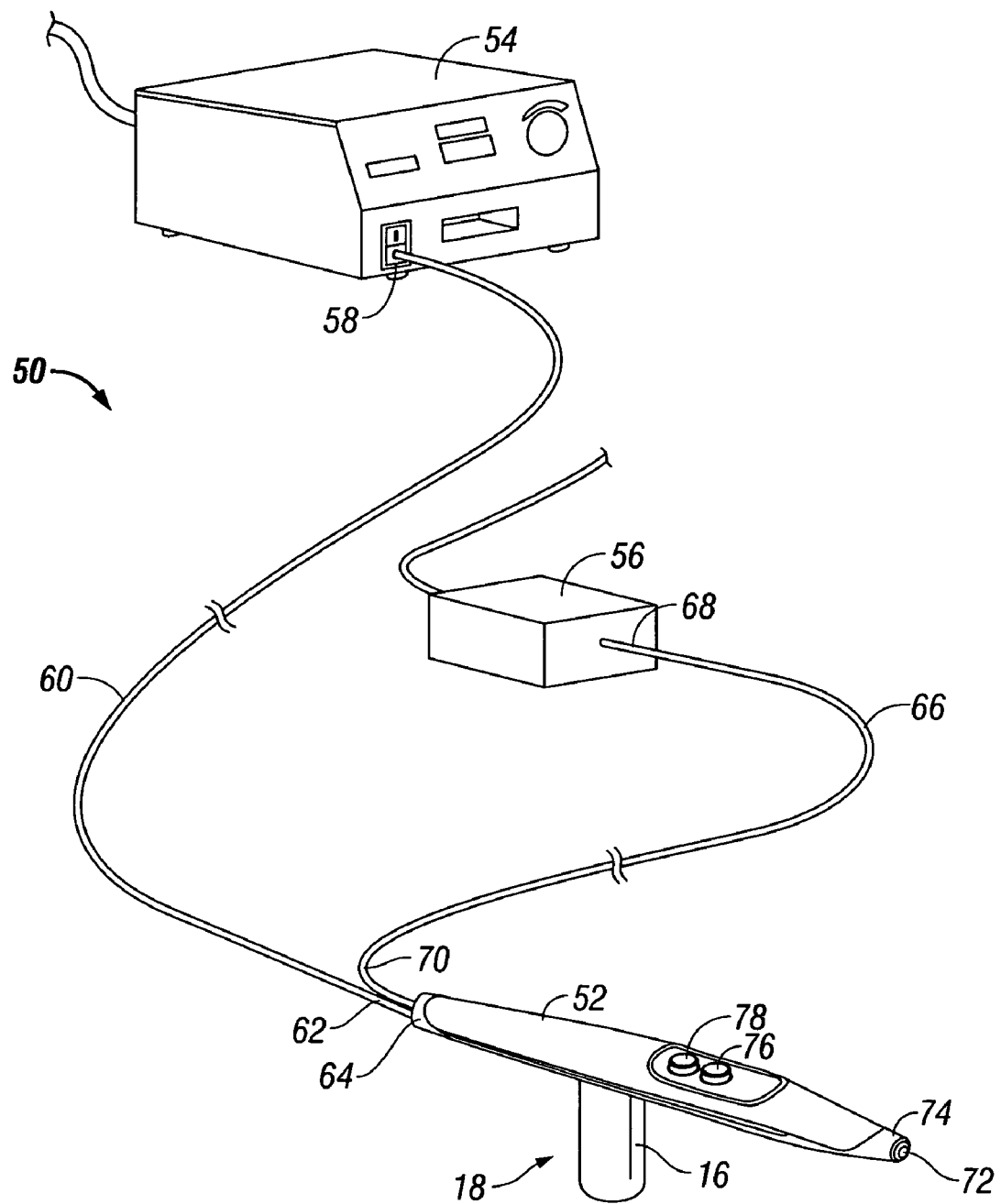
FIG. 5 is a perspective view of a disclosed wound mediating device incorporated into an electrosurgical instrument.

Referring now to FIG. 5, there is illustrated and electrosurgical instrument assembly 50 suitable for use with wound mediating supply 18. As noted above, wound mediating supply 18 may be provided as being attachable to a surgical instrument or may be a remote supply. Surgical instrument assembly 50 generally includes an electrosurgical instrument 52, a generator 54 and a pressure source 56. Generator 54 may be any suitable generator for supplying various energies to electrosurgical instrument 52, for example, dc current, ac current, microwave, etc. For example, generator 54 may be of the type available from Valleylab, Inc. of Boulder, Colo.—a division of Tyco Healthcare Group LP. A proximal end 58 of a transfer line 60 is connected to generator 54 while distal end 62 of transfer line 60 is connected to a proximal end 64 of electrosurgical instrument 52 to transfer energy generated from generator 54 to electrosurgical instrument 52.

Similarly, a pressure line 66 extends between pressure source 56 and electrosurgical instrument 52. Specifically a proximal end 68 of transfer line 66 is connected to pressure source 56 and a distal end 70 of pressure line 66 is connected to proximal end 64 of electrosurgical instrument 52. Pressure source 56, through pressure line 66, provides a source of fluid flow pressure to electrosurgical instrument 52. In this embodiment electrosurgical instrument 52 is a coagulation device. Pressure source 56 provides a gas, for example argon gas, to assist electrosurgical instrument 52 in the coagulation of tissue.

Electrosurgical instrument 52 includes a discharge port 72 located at a distal end 74 electrosurgical instrument 52. Discharge port 72 directs the electrical charge to tissue and allows for the presence of the argon gas flow to the tissue. In the illustrated embodiment, the first button 76 is provided on electrosurgical instrument 52 for controlling pressure source 56 while a second button 78 is provided on surgical instrument 52 for controlling the passage of slurry 14 (not explicitly shown) contained within canister 16 and into the argon gas flow stream.

In use, wound mediating supply 18 is initially attached to electrosurgical instrument 52. Thereafter, electrosurgical instrument 52 is utilized to coagulate tissue in known fashion. In conjunction with, or subsequent to, the coagulation of tissue second button 78 may be actuated to allow the gas stream flowing through electrosurgical instrument to draw slurry 14, (not explicitly shown) into the gas stream and propelled towards the tissue.

Figure 6A:
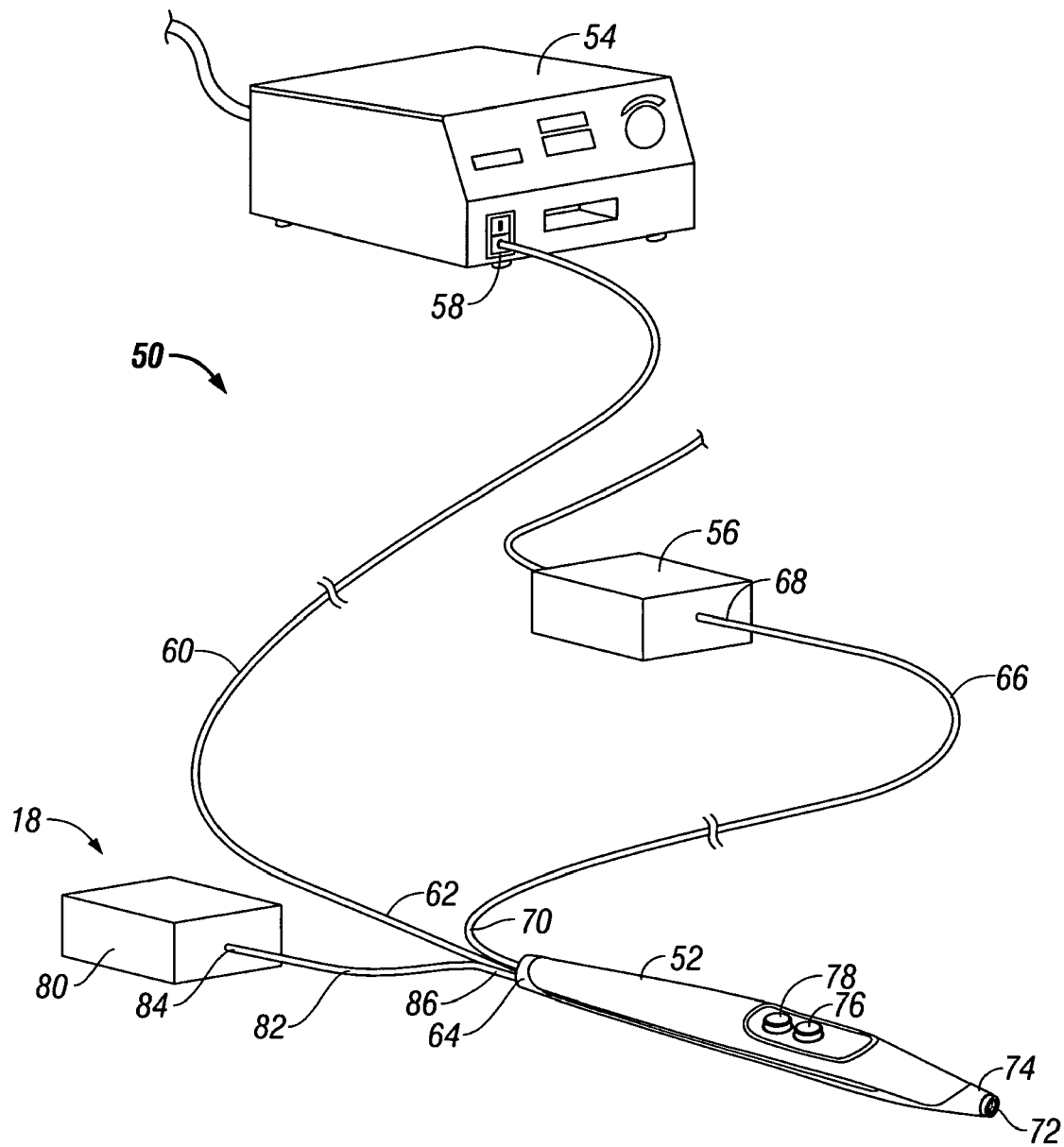
FIG. 6A is as prospective view of an alternate method of incorporating the disclosed wound mediating device into an electrosurgical instrument.

Referring now to FIG. 6A, and as noted hereinabove, wound mediating supply 18 may be provided as a removable canister 16 or may be a remote source. In this disclosed embodiment of wound mediating supply 18, slurry 14 (not explicitly shown) is contained within a wound mediating supply source 80. Wound mediating supply source 80 is connected to electrosurgical instrument 52 by a supply line 82. Specifically, a proximal end 84 of supply and 82 is connected to wound management supply source 80 while a distal end 86 of supply line 82 is connected to proximal end 64 electrosurgical instrument 52. This connection may be either removable or permanent with electrosurgical instrument 52.

In use, electrosurgical instrument assembly functions in substantially the same way as that described in an above with regard to electrosurgical instrument 50. As illustrated in FIG. 5, button 78 operates in substantially the same way to control the flow of slurry 14 (not explicitly shown) into the argon gas flow stream of the electrosurgical instrument and discharge it out discharge port 72 onto tissue.

Figure 6B:
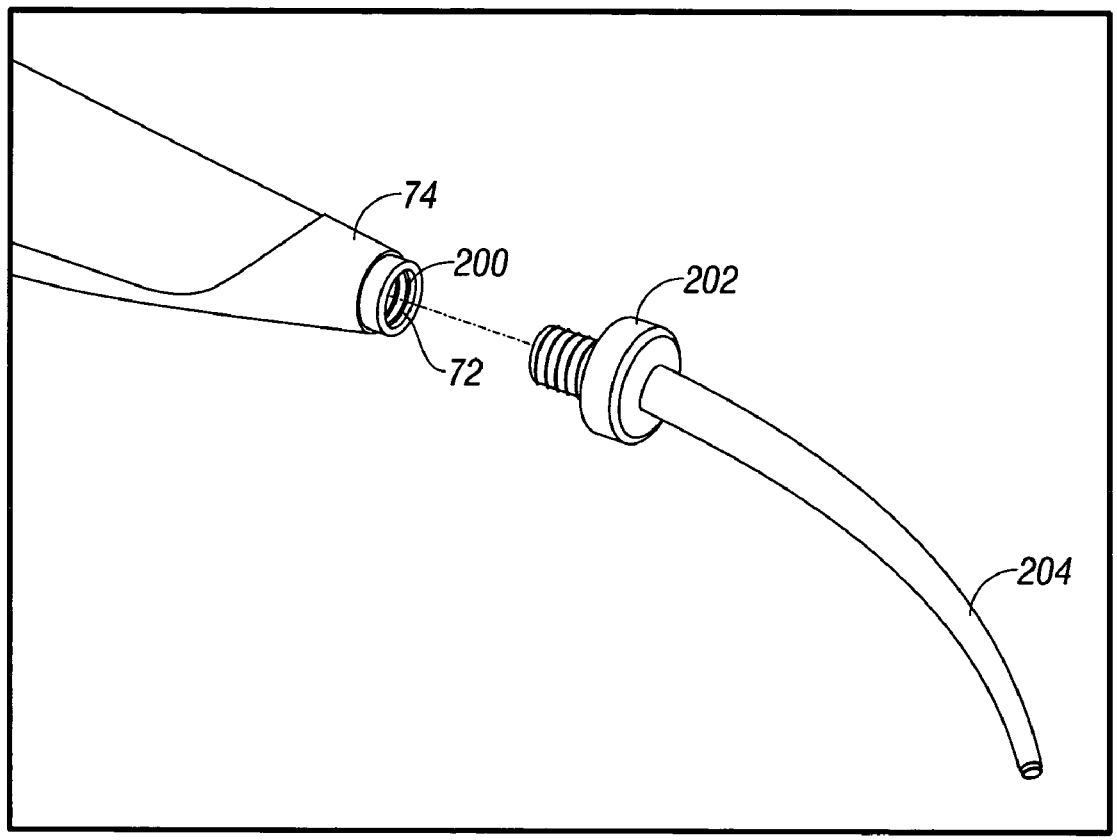
FIG. 6B is an enlarged view of an area of FIG. 6A showing a tube and attachment thereof.

In some embodiments, a tube may be attached to the discharge port 72 to facilitate delivery of the wound mediating substance. For example, referring now to FIG. 6B, an enlarged view of a capillary tube 204 is shown suitable for attachment to discharge port 72. Discharge port 72 has threads 200 along the inside edge thereof. A connector 202, having a tube 204 attached thereto, is shown suitable for attaching tube 204 to discharge port 72. Tube 204 can be any suitable tube for applying wound mediating substance to tissue. In some embodiments, tube 204 is a capillary tube for applying a thin stream of wound mediating substance to a wound.

Figure 7A:
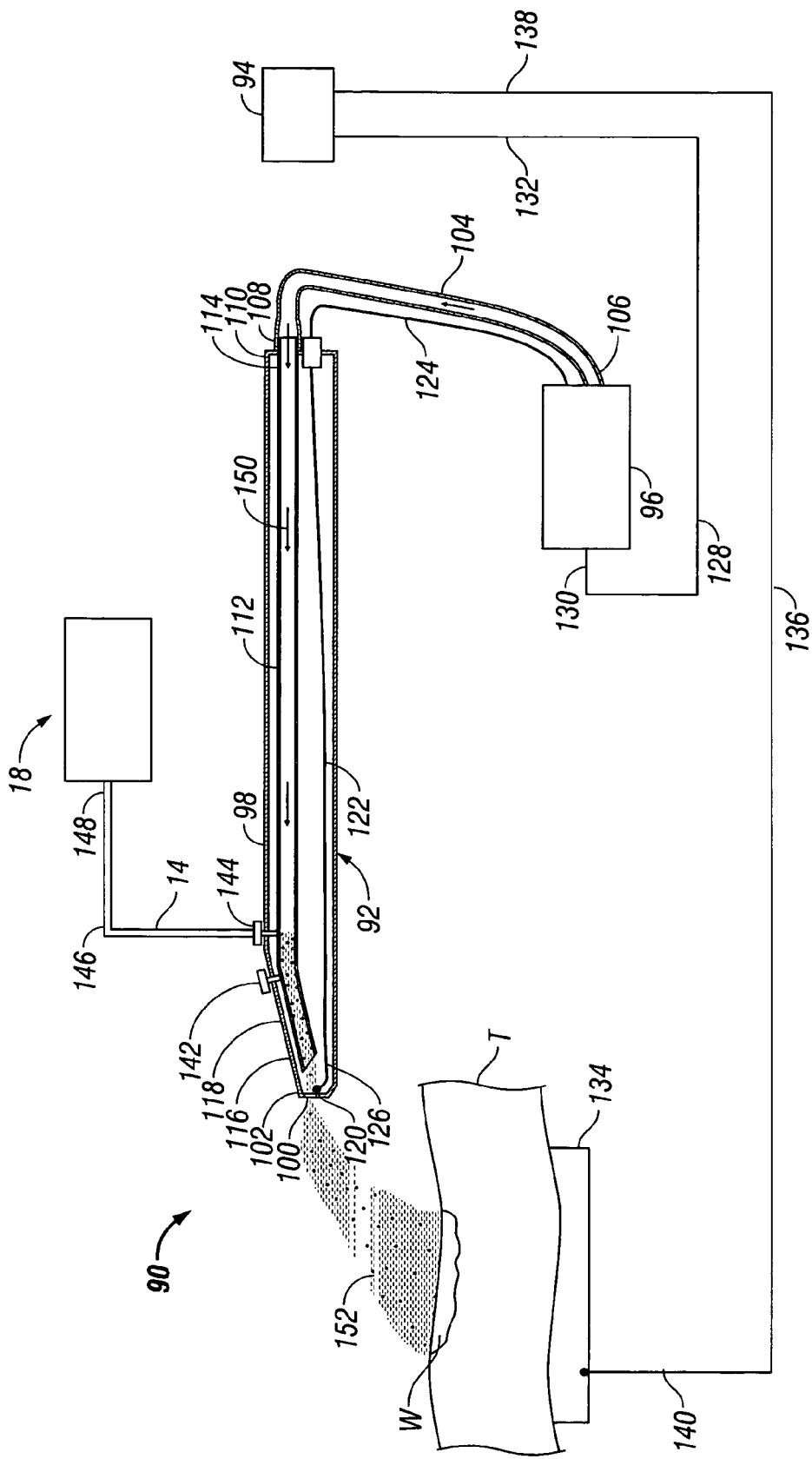
FIG. 7A is a side view of an alternate embodiment of an electrosurgical instrument propelling a wound mediating substance onto tissue.

Referring now to FIG. 7A, a further embodiment of an electrosurgical instrument assembly for use with wound mediating supply 18 will now be described. Electrosurgical instrument assembly 90 generally includes an electrosurgical instrument 92, a generator 94 and a pressure source 96. As noted hereinabove the disclosed generators may be of the type available from ValleyLab, Inc. of Boulder, Colo.—a division of Tyco Healthcare Group LP. Electrosurgical instrument 92 includes a housing 98 having a discharge port 100 located at a distal end 102 of housing 98. Discharge port 100 is provided to eject an ionized gas, such as an ionized argon gas, from electrosurgical instrument 92.

A flow tube 104 extends from pressure source 96 to electrosurgical instrument 92. A proximal end 106 of flow tube 104 is connected to pressure source 96 and a distal end 108 of flow tube 104 is connected to a proximal end 110 of housing 98. A second flow tube 112 extends through housing 98. A proximal end 114 of second flow tube 112 is connected to distal end 108 of flow tube 104. A discharge port 116 is located at a distal end 118 of second flow tube 112. Discharge port 116 is located proximally of second discharge port 100 in housing 98.

An active electrode 120 is positioned adjacent discharge port 100 in housing 98. Active electrode 120 is provided to ionize the argon gas supplied by pressure source 96 prior to being discharged from electrosurgical instrument 92. A transmission line 122 extends between pressure source 96 and electrosurgical instrument 92. A proximal end 124 extends into pressure source 96 and a distal end 126 terminates an active electrode 120. A second transmission line 128 is connected through pressure source 96 at its distal end to proximal end 124 of line 122. A proximal end 132 of second line 128 is connected to generator 94.

As is common with monopolar surgical instruments, electrosurgical instrument assembly 90 is also provided with a return pad 134 in contact with the tissue T. Line 136 extends from its proximal end 138, attached to generator 94, and has a distal end 140 connected to return pad 134.

Similar to previous embodiments electrosurgical instrument 92 is provided with a first button 142 to actuate electrosurgical instrument 92 and a second button 144 to control the transfer of wound mediating supply 18 into the argon gas flow stream. In this embodiment, wound mediating supply 18 is illustrated as a remote source of slurry 14. However, it is contemplated that this particular electrosurgical instrument could also use a detachable canister 16 that is directly affixed to electrosurgical instrument 92. A slurry line 146 extends from wound mediating supply 18 to electrosurgical instrument 92. Specifically, a proximal end 148 of slurry line 146 is connected to wound mediating supply 18. A distal end 144 of slurry line 146 is connected to electrosurgical instrument 92 through second button 144, which functions as a valve to permit slurry 14 into the argon gas flow stream.

In use, generator 94 provides an energy source to active electrode 120 to coagulate tissue at a wound site W. First button 142 is actuated to regulate the flow of an argon gas stream 150 through flow tube 112 towards discharge port 116. Active electrode 120 ionizes gas flow stream 150 as it is discharge towards wound W to coagulate tissue. As with prior embodiments, slurry 14 containing wound mediating substance 10 suspended therein by microbubbles 12 can be drawn into or otherwise inserted into gas flow stream 150 and directed towards tissue. Specifically, at the appropriate point during surgery, button 144 is depressed to meter the amount of slurry 14 flowing into gas flow stream 152. Slurry 14 may be introduced into gas stream 150 ahead of or behind the ionization of gas stream 152. As shown, once second button 144 is actuated to introduce slurry 14 into gas stream 150, a combined argon gas and atomized slurry 14 are propelled towards tissue to facilitate healing the tissue during the surgical procedure.

Figure 7B:
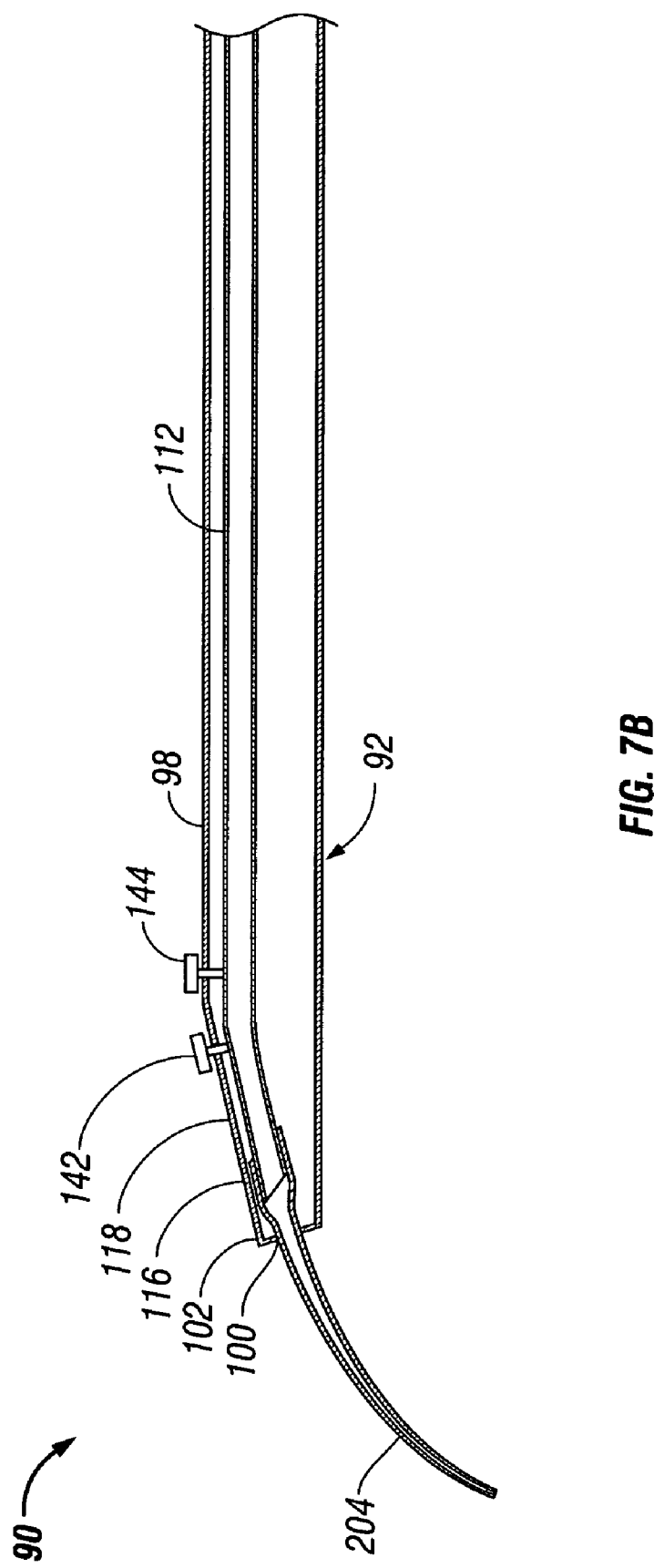
FIG. 7B is a side view of another alternate embodiment of an electrosurgical instrument with a discharge tube.

Referring to FIG. 7B, a further embodiment of an electrosurgical instrument assembly for use with wound mediating supply 18 will now be described. Electrosurgical instrument assembly 90 generally includes an electrosurgical instrument 92, having discharge port 100 located at a distal end 102 of housing 98. Discharge port 100 is provided to eject an ionized gas, such as an ionized argon gas, from electrosurgical instrument 92. As illustrated in FIG. 7B, a capillary tube 204 is shown connected to discharge port 116 of flow tube 112. In use, carrier material, wound mediating substance and gas may pass through the tube to deliver the wound mediating substance to a wound.

The present wound mediating substances and microbubbles and/or vehicles containing them in accordance with the present disclosure can be contacted with tissue is amounts sufficient to treat the tissue. As used herein the word "treat," "treating" or "treatment" refers to using the wound mediating substances, active ingredients and/or compositions of the present disclosure prophylactically to prevent wound formation or aggravation, or therapeutically to ameliorate an existing undesirable condition. A number of different treatments are now possible, which reduce and/or eliminate undesirable conditions.

As used herein "undesirable condition" refers to any detectable tissue manifestations caused by a wound or removal thereof. Such manifestations can appear due to a number of factors such as, for example, trauma and/or other diseased or dysfunctional state. Non-limiting examples of such manifestations include the development of cancer, inflammation, lesions, and/or other forms of tissue abnormality.

In embodiments, wound mediating substances for use in accordance with the present disclosure contain one or more active ingredients in an effective amount to improve undesirable conditions. As used herein "effective amount" refers to an amount of a wound mediating substance or composition having one or more active ingredients such as an antibacterial agent, an antifungal agent, an anti-inflammatory agent, an antimicrobial agents, an antiseptics, a chemotherapy agent, a coagulant, a hormone, a cancer tumor adjuvant, a local anesthetic, a pain mediator, a vasoconstrictor, a wound closing adhesive, a blood clotting factor, a growth factor, an interleukin, a cytokines, an inflammatory mediating factor, a chemokine and a matrix-metalloproteinase, and combinations of these active agents in amounts sufficient to induce a particular positive benefit to the wound or tissue adjacent thereto. The positive benefit can be health-related. In embodiments, the positive benefit is achieved by contacting tissue with a coagulation protein to promote clotting and closure of the excised tissue. In embodiments, the positive benefit is achieved by contacting tissue with a vasoconstrictor to reduce bleeding. In embodiments, the positive benefit is achieved by contacting tissue with a chemotherapeutic agent to kill cancerous cells. In embodiments, the positive benefit is achieved by sealing a wound with an adhesive. It is envisioned that numerous positive benefits can be achieved.

In some embodiments, the cancer tumor adjuvants and/or chemotherapeutic agents can be administered to a patient during a radiofrequency ablation procedure using the device and methods in accordance with the present disclosure. For example, standardized RF ablation can be combined with liposomal doxorubicin and one or more chemotherapeutic agents such as cisplatin, or 5-fluorouracil to treat one or more wounds or tumors. It is envisioned that any of the wound mediating substances described herein, can be used alone, or in combination to facilitate wound healing immediately after a standard RF ablation.

It will be understood that various modifications may be made to the embodiments disclosed herein. For example, and as noted above, the disclosed wound mediating supply and wound mediating devices may be utilized with other devices having fluid propellants to direct the wound mediating substances towards tissue. Further, the disclose slurry containing the wound mediating substance can be provided in a variety of containers, including those specifically and are integral to the surgical instrument associated with its use. Additionally, the wound mediating substances need not be encapsulated in microbubbles suspended in a slurry but may be provided for in other forms capable of being propelled towards tissue. Therefore, the above description should not be construed as limiting, but merely as exemplifications of particular embodiments. Those skilled in the art will envision other modifications within the scope and spirit of the claims appended hereto.

What is claimed is:
1. A wound mediating surgical instrument comprising:
an electrosurgical instrument having an internal chamber;
a fluid pressure source coupled to the electrosurgical instrument and in fluid communication with the internal chamber, the fluid pressure source operable to provide a fluid stream through the internal chamber;

an active electrode that receives an energy signal from a generator, wherein when the electrosurgical instrument is operated in a first mode the active electrode ionizes the fluid stream as the fluid stream flows toward a wound to coagulate tissue;

a wound mediating device coupled to the electrosurgical instrument and including a container, a slurry disposed within the container, a plurality of microbubbles suspended in the slurry and a wound mediating substance encapsulated in the microbubbles; and a valve for selectively introducing the slurry into the fluid stream of the internal chamber downstream of the fluid pressure source in a second operating mode where the active electrode ionizes the fluid stream as the fluid stream and slurry flow toward the wound, wherein the fluid stream is a gas.

2. The wound mediating surgical instrument as recited in claim 1, wherein the wound mediating device is removably attached to the surgical instrument.

3. The wound mediating surgical instrument as recited in claim 1, wherein the wound mediating substance is at least one of an antibacterial agent, an antifungal agent, an anti-inflammatory agent, an antimicrobial agents, an antiseptics, a chemotherapy agent, a coagulant, a hormone, a cancer tumor adjuvant, a local anesthetic, a pain mediator, a vasoconstrictor, a wound closing adhesive, a blood clotting factor, a growth factor, an interleukin, a cytokines, an inflammatory mediating factor, a chemokine and a matrix-metalloproteinase.

4. The wound mediating surgical instrument as recited in claim 1, wherein the microbubble is at least one of a liposome, a micelle, and a microsphere.

5. The wound mediating surgical instrument as recited in claim 3, further comprising a capillary tube connected to a distal end of the electrosurgical instrument, wherein the capillary tube applies a thin stream to the wound.

6. The wound mediating surgical instrument as recited in claim 5, wherein the fluid stream is argon.

7. A method of treating a wound during surgery comprising the steps of:

encapsulating a wound mediating substance in microbubbles;

suspending the microbubbles in a slurry;

storing the slurry in a container;

supplying a pressurized gas into a fluid stream;

activating an electrode to ionize the fluid stream and coagulate tissue at a wound site;

selectively drawing the slurry out of the container and into the fluid stream; and directing the fluid stream towards a wound in tissue.

8. The method as recited in claim 7, wherein the pressurized gas is supplied through an electrosurgical instrument.

9. The method of claim 7, wherein the step of selectively drawing the slurry is controlled by a valve.

10. The method according to claim 7, wherein the pressurized gas and the slurry are operatively combinable within a wound mediating instrument.

11. The method according to claim 7, wherein the wound mediating substance is at least one of a wound closing adhesive, a blood clotting factor, a growth factor, an interleukin, a cytokines, an inflammatory mediating factor, a chemokine and a matrix-metalloproteinase.

12. The method according to claim 7, wherein the source of pressurized gas is argon.

* * * * *